United States Patent [19]
Zimmerman et al.

[11] Patent Number: 5,859,058
[45] Date of Patent: Jan. 12, 1999

[54] NITRIC OXIDE SYNTHASE INHIBITORS FOR INHIBITING THE PRODUCTION OF AIRWAY MUCAS

[75] Inventors: Thomas Paul Zimmerman, Raleigh; Luis Molina, Chapel Hill, both of N.C.

[73] Assignee: Glaxo Wellcome Inc., Research Triangle Park, N.C.

[21] Appl. No.: 765,547

[22] PCT Filed: Jul. 13, 1995

[86] PCT No.: PCT/GB95/01657

§ 371 Date: Apr. 11, 1997

§ 102(e) Date: Apr. 11, 1997

[87] PCT Pub. No.: WO96/02245

PCT Pub. Date: Feb. 1, 1996

Related U.S. Application Data

[63] Continuation of PCT/GB95/01657, Jul. 13, 1995, which ia a continuation of Ser. No. 275,167, Jul. 14, 1994, abandoned.

[51] Int. Cl.⁶ .................................................. A61K 31/195
[52] U.S. Cl. ............................................... 514/565
[58] Field of Search ............................................... 514/565

[56] References Cited

U.S. PATENT DOCUMENTS

| | | |
|---|---|---|
| 5,028,627 | 7/1991 | Kilbourn et al. . |
| 5,317,040 | 5/1994 | Goldman . |
| 5,358,969 | 10/1994 | Williamson et al. .................... 514/632 |

OTHER PUBLICATIONS

"Neural nitric oxide synthase is localized in extrinsic nerves regulating perireceptor processes in the chemosensory nasal mucosae of rats and humans", J. Comp. Neurol., vol.. 345, No. 1, pp. 125–138, Jul. 1, 1994.

"TNF–alpha stimulates mucin secretion and gene expression in airway epithelium in vitro", Chest, vol., 107, No. 3, pp. 133S–135S, Mar. 3, 1995.

"Impairment of endothelium–dependent pulmonary artery relaxation in chronic obstructive lung disease", N. Engl. J. Med., vol. 324, No. 22, pp. 1539–1547 (1991).

*Primary Examiner*—Raymond Henley, III
*Attorney, Agent, or Firm*—Lorie Ann Morgan

[57] ABSTRACT

The use of an NO synthase inhibitor, for example L-NMMA, in inhibiting the production of airway mucus secretion, e.g., in cystic fibrosis, chronic bronchitis and emphysema, is disclosed.

6 Claims, No Drawings

NITRIC OXIDE SYNTHASE INHIBITORS FOR INHIBITING THE PRODUCTION OF AIRWAY MUCAS

This application is filed pursuant to 35 U.S.C. § 371 as a United States National Phase Application of International Application No. PCT/GB95/01657 filed Jul. 13, 1995 which is a continuation of U.S. Ser. No. 08/275,167 Filed Jul. 14, 1994 (Abandoned).

The present invention relates to the use of nitric oxide synthase inhibitors in inhibiting secretion and/or production of airway mucus, in particular in treating chronic bronchitis, cystic fibrosis and bronchorrhea.

In cystic fibrosis several functions of airway epithelia are abnormal including thickened airway surface fluid. This thickened airway fluid contributes to the recurrent pulmonary infections and loss of ventilatory function that occur in cystic fibrosis. Retained airway secretions are also known to contribute to the morbidity of other pulmonary diseases such as asthma and chronic obstructive pulmonary disease.

The therapeutic goal in cystic fibrosis and other pulmonary diseases in which the water content of the mucus is altered is to remove retained secretions from the lungs. For example, the use of aerosolised amiloride to facilitate the removal of retained mucus secretions is described in U.S. Pat. No. 4,501,729. Amiloride appears to block $Na^+$ reabsorption by airway epithelial cells, and therefore inhibits water absorption from mucus.

A different therapeutic approach is to increase the water content of the airway surface liquid by modulating the activity of chloride channels. An example of this is the administration of ATP or UTP, which appear to induce hydrated mucus secretions by stimulating chloride secretion from respiratory epithelial cells. See, e.g., C.Stock, Breathing Easier: A promising Treatment for Cystic Fibrosis, *Endeavors*, 10, 10–11 (Fall 1992) (Published by the Office of Research Services, The University of North Carolina at Chapel Hill).

It has subsequently been found that administering a nitric oxide synthase inhibitor is beneficial in inhibiting the production and/or secretion of airway mucus.

Accordingly, the present invention provides a method of inhibiting the production and/or secretion of airway mucus which comprises administering to a mammal in need thereof an effective amount of an NO synthase inhibitor to the lungs of the mammal.

In a further aspect, the present invention provides a method of combating cystic fibrosis which comprises administering to a mammal in need thereof an effective amount of an NO synthase inhibitor to the mammal.

In a yet further aspect, the present invention provides a method of combating excessive mucus production in chronic bronchitis which comprises administering to a mammal in need thereof an effective amount of an NO synthase inhibitor to the mammal.

In a still further aspect the present invention provides a method of combating emphysema which comprises administering to a mammal in need thereof an effective amount of an NO synthase inhibitor to the mammal.

The method of the present invention may further comprise the step of concurrently administering a further active agent useful in improving mucociliary clearance of airway mucus, for example a sodium channel blocker, such as amiloride, in an amount effective to inhibit the reabsorption of water from lung mucus secretions, or a lantibiotic such as duramycin, or a nucleotide such as adenosine triphosphate (ATP) or uridine triphosphate (UTP) in an amount effective to facilitate hydration and clearance of airway mucus.

In the alternative there is provided the use of a NO synthase inhibitor in the manufacture of a medicament to facilitate mucus clearance The present invention also provides the use of an NO synthase inhibitor for the manufacture of a medicament for the inhibition of the production of airway mucus in a patient in need of such treatment. Suitably the patient is suffering from cystic fibrosis or chronic bronchitis.

Suitably the NO synthase inhibitor is an arginine derivative such as those described in U.S. Pat. No. 5,028,627 and preferably it is $N^G$-monomethyl-L-arginine (L-NMMA) or a salt thereof.

L-NMMA is available from Sigma Chemical Company Limited, Fancy Road, Poole, Dorset BH17 7NH, England.

Many NO synthase inhibitors, for example L-NMMA, are capable of forming salts. Thus, the present invention includes NO synthase inhibitors in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of NO-synthase inhibitors can be made by reacting the appropriate compound in the form of the free base with the appropriate acid.

Whilst it may be possible for the NO-synthase inhibitors to be administered as the raw chemical, it is preferable to present them as a pharmaceutical formulation. According to a further aspect, the present invention provides a pharmaceutical formulation comprising the NO synthase inhibitor or a pharmaceutically acceptable salt or solvate thereof, together with one or more pharmaceutically acceptable carriers therefor and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), intranasal, inhaled, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association the NO-synthase inhibitor or a pharmaceutically acceptable salt or solvate thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example sublingually, include lozenges comprising the active ingredient in a flavoured basis such as sucrose and acacia or tragacanth, and pastilles comprising the active ingredient in a basis such as gelatin and glycerin or sucrose and acacia.

Formulations suitable for pulmonary administration via the buccal cavity are presented such that particles containing the active ingredient and desirably having a diameter in the range 0.5 to 7 microns are delivered into the bronchial tree of the recipient. Such formulations may be in the form of finely comminuted powders which may conveniently be presented in a pierceable capsule, for example of gelatin, for use in an inhalation device, or as a self-propelling formulation (also referred to as an aerosol formulation) comprising the active ingredient a suitable liquid or gaseous propellant and optionally other ingredients such as a surfactant and/or a solid diluent. Suitable liquid propellants include propane and the chlorofluorocarbons, and suitable gaseous propellants include carbon dioxide. Suitable surfactants include sorbitan trioleate (which is available for example under the trade name "Arlacel 85"), Polysorbate 20 and oleic acid. Self-propelling formulations may also be employed wherein the active ingredient is dispensed in the form of droplets of solution or suspension. The self-propelling formulation typically contains from 0.05 to 20 mg/ml e.g. 0.1 to 5 mg/ml of the active ingredient.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility, the active ingredient may be in the form of a solution or suspension for use in an atomiser or nebuliser whereby an accelerated airstream or ultrasonic agitation is employed to produce a fine droplet mist for inhalation. Such solutions or suspensions may comprise, in addition to the naphthoquinone and solvent(s), optional ingredients such as surfactants. Suitable surfactants include those described above for self-propelling formulations. The solution or suspension typically contains from 500 $\mu$M to 100 mM e.g. 0.5 mM to 25 mM of the active ingredient. When a suspension of the active ingredient is employed, this compound is preferably in finely divided form, e.g. in micronised form.

Formulations suitable for nasal administration include presentations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of the active ingredient in aqueous or oily solution or suspension.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The NO synthase inhibitors of the invention may be administered orally, or via injection at a dose of from 1 to 100 mg/kg per day. When the NO synthase inhibitors are given by injection, this will normally be in the form of an intravenous bolus or by infusion, preferably the latter. The dose range for adult humans is generally from 70 mg to 2.5 g/day and preferably 150 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

In a further embodiment of the invention, the NO synthase inhibitors are administered by aerosol to the lungs of a subject in an amount sufficient to achieve concentrations of NO synthase inhibitor on the airway surface liquid of the patient of about 5 $\mu$Moles/litre to 1000 $\mu$Moles/litre, preferably 100 $\mu$Moles/litre to 500 $\mu$Moles/litre.

The dose of the NO synthase inhibitor will vary according to the potency of the inhibitor, its selectivity for the different forms of the enzyme and the dose at which adverse pharmacological effects become evident. The person skilled in the art will take these factors into account when determining the dose of inhibitor to be administered.

The present invention will now be described by way of example only.

EXAMPLE

SPOC-1 Cell Line Synopsis

The experimental mode used is the SPOC-1 cell line, a mucin-secreting cell line that results from a spontaneous transformation in a primary culture of rat tracheal cells. SPOC-1 cells seeded in a rat tracheal xenograft and implanted into a nude mouse differentiate into a pseudo-stratified epithelium in which the upper layer of cells possesses a goblet cell phenotype, including the possession of 1+μm granules. In culture either on plastic or on Transwell-Col (Costar) permeable supports, the cells differentiate over a period of 9 to 12 days into a multilayered (3 to 4 layers) epithelium in which outer layers contain material which stains positive with PAS. A PAS-positive glycoconjugate with a molecular weight appropriate for mucin ($>10^6$ daltons) is detected by gel electrophoresis of SPOC cell lysate and perfusate; and SPOC cells stain positive with an monoclonal antibody specific to purified rat mucin.

An enzyme-linked lectin binding assay (ELLA-is analogous to ELISA but uses a lectin instead of an antibody) that is sensitive to the ng/ml range and a perfusion system for cultures growing on both plastic (12-well plates) and TCol supports has been developed.

Testing Procedure

SPOC-1 cells grown on plastic are employed as a convenient experimental model to test chemical compounds for inhibitory or stimulatory effects on mucin secretion. Each compound is initially tested, on duplicate cultures in short-term exposures, for potential effects on both baseline and ATP-stimulated secretion over a range of 12 doses (including a control). 12-well plates are perfused (each well independently), and after a suitable equilibration period, 5 min fractions collected for baseline (30 min), baseline+test compound (60 min), and ATP+test compound (60 min). A level of ATP at its $EC_{50}$, 10 μM is used, so potential stimulatory effects on regulated mucin secretion are detected with the compounds of interest; if the primary interest is in the inhibitory direction, then a maximal ATP dose, 100 or 300 μM is used.

The fractions collected are assessed for mucin content by ELLA, and the data analysed as follows, using standard spreadsheet software (MS Excel). Data from duplicate samples is averaged. The time course of mucin secretion for each perfused culture is plotted, and the levels of mucin secretion assessed for each period (baseline, baseline+compound, and compound+ATP). Calculating the data relative to baseline rates, dose-response curves for the baseline+compound and the compound+ATP periods are constructed. These plots are analysed for inhibitory or stimulatory effects by the compounds of interest, by comparing data for each baseline+compound period to the preceding baseline, and for each compound+ATP period to the preceding baseline+compound period.

Scientists from North Carolina State University have examined the mechanism involved in stimulation of mucus secretion. Stimulation of mucus secretion was completely blocked by L-NMMA at a dose of 0.1–1.0 mM, but not by D-NMMA, indicating the role of nitric oxide in mucus secretion (K. B. Adler et al., Chest, 107(3), 133S–135S, 1995).

We claim:

1. A method of inhibiting the production of airway mucus in a patient in need of such treatment which comprises administering an effective amount of an NO synthase inhibitor to the lungs of the mammal.

2. The method according to claim 1, wherein said NO synthase inhibitor is L-NMMA.

3. The method according to claim 1, wherein said method further comprises administering said NO synthase inhibitor in conjunction with a further active ingredient useful in improving mucociliary clearance of airway mucus.

4. The method according to claim 1, wherein said method further comprises combating cystic fibrosis.

5. The method according to claim 1, wherein said method further comprises combating excessive mucus production in chronic bronchitis.

6. The method according to claim 1, wherein said method further comprises combating emphysema.

* * * * *